(12) United States Patent
Kim

(10) Patent No.: US 8,840,554 B2
(45) Date of Patent: Sep. 23, 2014

(54) ULTRASONIC 3-DIMENSIONAL IMAGE RECONSTRUCTION METHOD AND ULTRASONIC WAVE SYSTEM THEREOF

(75) Inventor: Min Woo Kim, Seoul (KR)

(73) Assignee: Samsung Medison Co., Ltd., Gangwon-Do (KR)

( * ) Notice: Subject to any disclaimer, the term of this patent is extended or adjusted under 35 U.S.C. 154(b) by 733 days.

(21) Appl. No.: 12/938,129

(22) Filed: Nov. 2, 2010

(65) Prior Publication Data

US 2011/0144497 A1    Jun. 16, 2011

(30) Foreign Application Priority Data

Dec. 14, 2009   (KR) .................. 10-2009-0123798

(51) Int. Cl.
*A61B 8/00*    (2006.01)

(52) U.S. Cl.
USPC ........................... 600/437; 600/407; 600/443

(58) Field of Classification Search
USPC ........................................ 600/407, 437–472
See application file for complete search history.

(56) References Cited

U.S. PATENT DOCUMENTS

| | | | |
|---|---|---|---|
| 5,628,320 A * | 5/1997 | Teo ................................ | 600/443 |
| 2002/0131546 A1 | 9/2002 | Oikawa | |
| 2003/0149357 A1* | 8/2003 | Liu ................................ | 600/437 |
| 2004/0254460 A1* | 12/2004 | Burcher et al. .............. | 600/437 |
| 2006/0084869 A1 | 4/2006 | Kim et al. | |
| 2006/0102846 A1 | 5/2006 | Manjeshwar et al. | |
| 2009/0123048 A1 | 5/2009 | Leroux et al. | |
| 2009/0141995 A1* | 6/2009 | Chakraborty et al. ........ | 382/248 |

FOREIGN PATENT DOCUMENTS

| | | |
|---|---|---|
| JP | 2002-224097 A | 8/2002 |
| KR | 10-2006-0034003 | 4/2006 |
| WO | WO 02/48734 A2 | 6/2002 |
| WO | WO 2007/027703 A2 | 3/2007 |
| WO | 2009/082531 A1 | 7/2009 |

OTHER PUBLICATIONS

Korean Notice of Allowability, issued in Korean Patent Application No. 10-2009-0123798, dated Sep. 15, 2011.
European Search Report issued in European Patent Application No. 10161016.0-1265, mailed Oct. 6, 2010.
Japanese Office Action issued in Japanese Patent Application No. 2010-181075 dated Apr. 8, 2014, with English Translation.

* cited by examiner

*Primary Examiner* — James Kish
(74) *Attorney, Agent, or Firm* — McDermott Will & Emery LLC

(57) ABSTRACT

Disclosed are systems and methods for reconstructing a three-dimensional ultrasound image. The method may include generating a two-dimensional image having various directivities in a frequency space based on plane wave data; manipulating the generated two-dimensional image to generate three-dimensional image data; and reconstructing a three-dimensional ultrasound image by performing an inverse fast Fourier transformation on the three-dimensional image data. The method may further include using a fast Fourier transformation, a lookup table, back-projection, filtering, de-noising, compressed sensing, and/or the projection-slice theorem.

19 Claims, 5 Drawing Sheets

ULTRASONIC 3-DIMENSIONAL IMAGE RECONSTRUCTION METHOD AND ULTRASONIC WAVE SYSTEM THEREOF

CROSS-REFERENCE TO RELATED APPLICATION

This application claims the benefit of Korean Patent Application No. 10-2009-0123798, filed on Dec. 14, 2009, in the Korean Intellectual Property Office, the disclosure of which is incorporated herein by reference.

BACKGROUND OF THE INVENTION

1. Field of the Invention

The present invention relates to systems and methods for reconstructing a three-dimensional ultrasound image.

2. Description of the Related Art

Previously-known ultrasound systems may be used to display three-dimensional (3D) ultrasound images. However, these images may not be sufficiently accurate when the system displays, for example, a lesion or tissue of a patient during medical operations such as diagnosis, biopsy, and surgery.

Ultrasound systems typically employ a probe having one or more transducers that send acoustic pulses into a material. The pulses are reflected back to the probe after the pulses impinge upon materials having different acoustical characteristics. A subcutaneous body structure may be imaged based on the strength of the received pulses and time elapsed between transmission and receipt of the pulses. Pulse Repetition Frequency (PFR) is the number of times per second that a pulse is transmitted (e.g., transmitted from the probe). A high Pulse Repetition Frequency (PRF) scheme may be employed by the ultrasound system to generate three-dimensional ultrasound images of a rapidly moving object such as a heart of a human being in real time. Previously-known ultrasound systems have employed high PRF techniques using plane waves that produce a plurality of scan-line data at one time. However, ultrasound systems that use these techniques may generate too much noise and, consequently, display low resolution images.

Additionally, previously-known ultrasound systems may reconstruct three-dimensional images by interpolating two-dimensional image data generated by the system. This data may include information indicating how much of the total energy from the ultrasound system is radiating in a particular direction, known as directivity. Still, the systems that reconstruct three-dimensional images using these techniques are only capable of displaying relatively low resolution images due to noise generated by the system and limitations on the number of two-dimensional images that may be interpolated.

SUMMARY OF THE INVENTION

An aspect of the present invention provides an ultrasonic three-dimensional (3D) image reconstruction method and an ultrasonic wave system thereof, which may obtain ultrasonic 3D images having a high resolution.

According to an aspect of the present invention, an ultrasonic three-dimensional (3D) image reconstruction method, includes: forming, from data of ultrasound plane waves transmitted from a plurality of directions, a two-dimensional (2D) image having various directivities in a frequency space; forming 3D image data by applying a back-projection scheme to data of the 2D image; and reconstructing a 3D image by performing an inverse fast Fourier transformation (IFFT) on the 3D image data.

According to another aspect of the present invention, an ultrasonic wave system, includes: a 2D image formation unit to acquire, from ultrasound plane waves transmitted from a plurality of directions, a 2D image having various directivities in a frequency space; a 3D image reconstruction unit to acquire 3D image data by applying a back-projection scheme to data of the 2D image, and to reconstruct a 3D image by performing an inverse fast Fourier transformation (IFFT) on the 3D image data; and a display unit to display the 3D image.

According to another aspect of the present invention, a method for reconstructing a three-dimensional ultrasound image includes generating a two-dimensional image having various directivities in a frequency space based on plane wave data; manipulating the generated two-dimensional image to generate three-dimensional image data; and reconstructing a three-dimensional ultrasound image by performing an inverse fast Fourier transformation on the three-dimensional image data.

Generating a two-dimensional image may include generating the two-dimensional image using a fast Fourier transformation and/or a lookup table.

Manipulating the generated two-dimensional image may include back-projecting the generated two-dimensional image to generate the three-dimensional image data and/or filtering the generated two-dimensional image before back-projecting.

Reconstructing a three-dimensional ultrasound image may include applying de-noising and/or compressed sensing to the generated the three-dimensional image data.

In a preferred embodiment, the method includes, prior to the generating, manipulating, and reconstructing steps, transmitting plane wave data from a plurality of directions via an ultrasound probe.

The method may include displaying the reconstructed three-dimensional ultrasound image.

The method may be implemented using a computer-readable medium.

According to another aspect of the present invention, an ultrasound system includes a two-dimensional image formation unit configured to generate a two-dimensional image having various directivities in a frequency space based on plane wave data; a three-dimensional image reconstruction unit configured to manipulate the generated two-dimensional image to generate three-dimensional image data and reconstruct a three-dimensional ultrasound image by performing an inverse fast Fourier transformation on the three-dimensional image data.

The two-dimensional image formation unit may use a fast Fourier transformation and/or a lookup table to generate the two-dimensional image.

The three-dimensional image reconstruction unit may use back-projection to manipulate the generated two-dimensional image and may filter the generated two-dimensional image before using the back-projection. The three-dimensional image reconstruction unit may apply compressed sensing and/or de-noising to the three-dimensional image data to reconstruct the three-dimensional ultrasound image.

The system may include an ultrasound probe configured to generate the plane wave data and transmit the plane wave data to the two-dimensional image formation unit and may include a display unit configured to display the reconstructed three-dimensional ultrasound image.

According to another aspect of the present invention, a computer readable medium includes instructions that cause a computer processor to generate a two-dimensional image having various directivities in a frequency space based on plane wave data; manipulate the generated two-dimensional image to generate three-dimensional image data; and reconstruct a three-dimensional ultrasound image by performing an inverse fast Fourier transformation on the three-dimensional image data.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
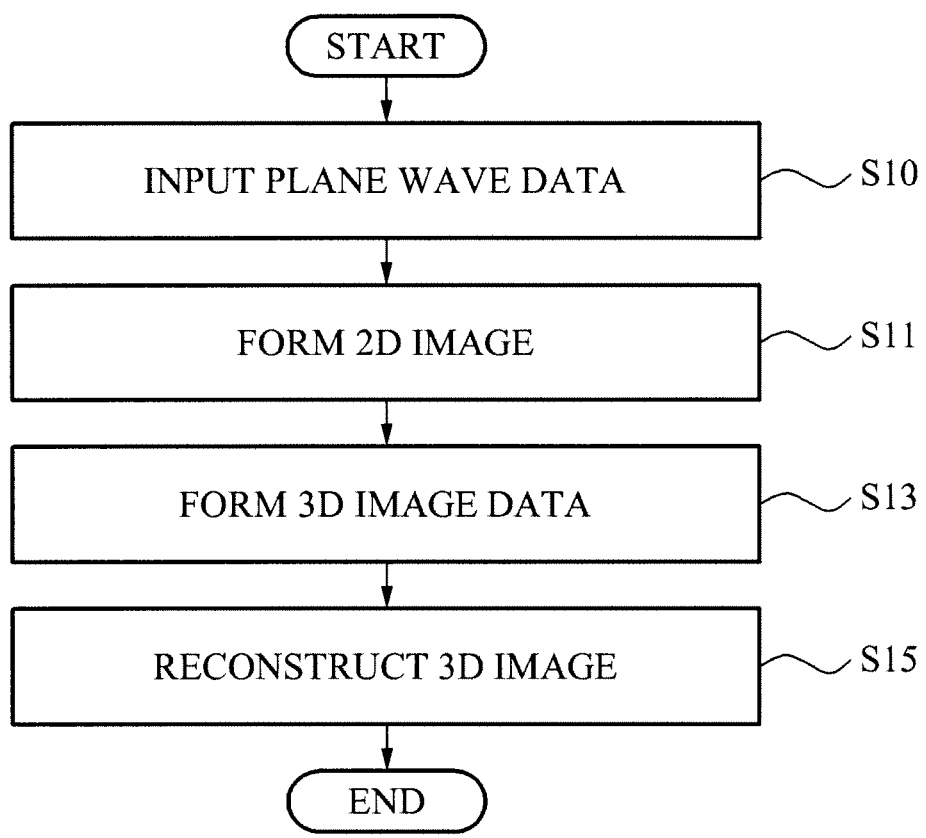
FIG. 1 is a flowchart illustrating a method for reconstructing a three-dimensional ultrasound image according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Embodiments of the present invention include systems and methods for reconstructing three-dimensional ultrasound images. The ultrasound system may include a probe, e.g., a 3D mechanical probe or a multi-dimension electronic array probe. The probe is placed on a subject's epidermis near the target area to obtain data (e.g., plane wave data) regarding the subcutaneous structures to be imaged.

FIG. 1 is a flowchart illustrating a method for reconstructing a three-dimensional ultrasound image according to an embodiment of the present invention.

First, at step S10, plane wave data transmitted from a plurality of directions by a probe is inputted.

Then, at step S11, two-dimensional images are generated using the transmitted plane wave data. The generated two-dimensional images may have various directivities in a frequency space. The two-dimensional images may be generated using, for example, a fast Fourier transformation (FFT) or a lookup table as described below.

Figure 2:
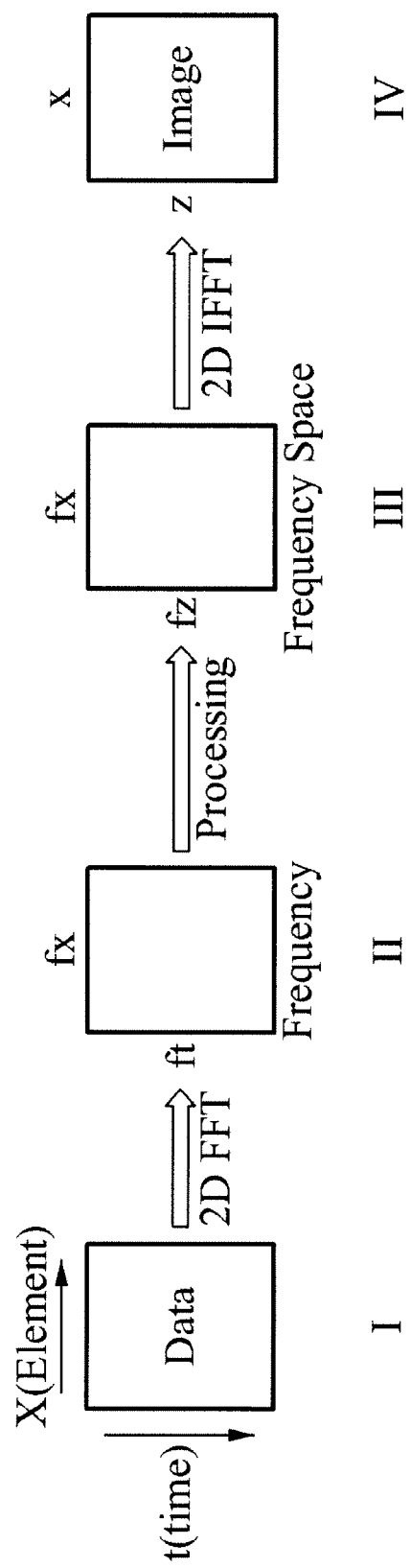
FIG. 2 is a conceptual diagram illustrating an exemplary step for generating a two-dimensional image using a Fast Fourier Transformation (FFT) according to an embodiment of the present invention.

FIG. 2 is a conceptual diagram illustrating an exemplary step S11 for generating a two-dimensional image using a fast Fourier transformation (FFT) according to an embodiment of the present invention. A FFT is an algorithm used to compute the discrete Fourier transform (DFT) and its inverse. The DFT is a frequency domain representation of the original function, i.e., a function in the time domain.

At stage I, the plane wave data from the probe may be a function in the time domain and arranged on an X-axis (element) and a t-axis (time). Between stages I and II, a FFT may be performed on the plane wave data to obtain values of 'fx' and 'ft' in a frequency domain, i.e., the DFT, as illustrated in stage II. Next, between stages II and III, the obtained values of 'fx' and 'ft' are processed to convert the values of 'fx' and 'ft' into values of 'fx' and 'fz' of an x-axis and an z-axis, respectively, as illustrated in stage III. Processing may include performing a phase shift operation, an interpolation operation, and/or a remapping operation on the obtained values. Finally, between stages III and IV, an inverse fast Fourier transformation (IFFT) may be performed on the converted values ('fx' and 'fz') to generate two-dimensional images, as illustrated in stage IV.

Figure 3:
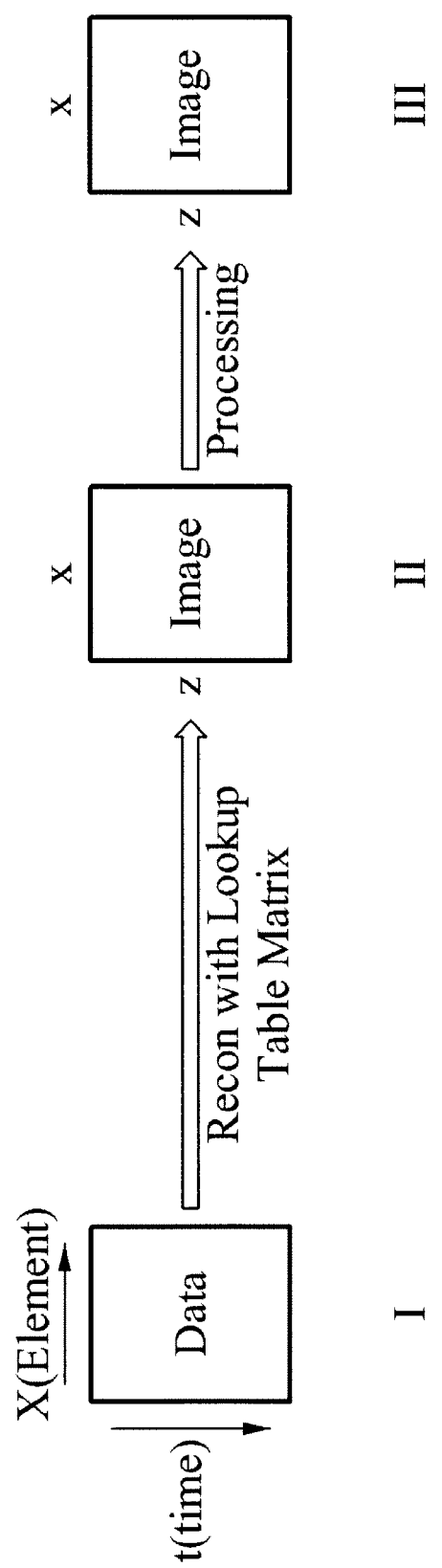
FIG. 3 is a conceptual diagram illustrating an exemplary step for generating a two-dimensional image using a lookup table according to an embodiment of the present invention.

FIG. 3 is a conceptual diagram illustrating an exemplary step S11 for generating a two-dimensional image using a lookup table according to another embodiment of the present invention. At stage I, the plane wave data from the probe may be arranged in the X-axis and the t-axis in the same manner described with respect to stage I of FIG. 2. Between stages I and II, an Rx dynamic focusing operation is performed on the plane wave data based on a lookup table matrix to generate image data, as illustrated in stage II. Dynamic focusing may be used to control the axial position of the focus of an ultrasound signal generated by the probe and may control the phase of signals detected by the transducer array within the probe. A lookup table may be used to transform input data, e.g., plane wave data, into a more desirable output format, e.g., image data. The transformation may take place using lookup table techniques known in the art. Next, between stages II and III, the image data are processed to generate two-dimensional images, as illustrated in stage III. Processing may include performing a phase shift operation, an interpolation operation, and/or a remapping operation on the image data.

Referring back to FIG. 1, at step S13, three-dimensional image data may be generated by manipulating the generated two-dimensional image. Manipulating may include, for example, back-projecting and/or filtering the generated two-dimensional image to generate the three-dimensional image data.

Back-projection, as used in the context of image processing, takes a function defined on each line in a plane and projects it back over the line to produce an image. Back-projection is also known as a dual Radon transform. For example, a function defined on each line in the generated two-dimensional image may be projected back over the image to generate the three-dimensional image data. As another example, the three-dimensional image data, referred to as 'x', may be calculated using Equations 1 and 2 where 'y' is a set of two-dimensional image data having various directivities and 'A' is a projection matrix.

$$Y = Ax. \qquad \text{[Equation 1]}$$

'x' may be calculated by multiplying the inverse function of 'A' by 'y', as illustrated in Equation 2.

$$\bar{x} = A^{-1}y = A^T F y. \qquad \text{[Equation 2]}$$

As described above, manipulating may include filtering the generated two-dimensional image to generate the three-dimensional image data. Filtering means suppressing some unwanted feature, e.g., noise, in a signal, e.g., the generated two-dimensional image. A filter known in the art of signal processing may be used to filter the two-dimensional image. In a preferred embodiment, filtering occurs before back-projecting.

Then, at step S15, a three-dimensional ultrasound image is reconstructed from the three-dimensional ultrasound data.

Reconstructing a three-dimensional ultrasound image may include, for example, back-projecting, filtering, applying compressed sensing, de-noising, using a projection-slice theorem, and/or performing an inverse fast Fourier transformation on the three-dimensional image data. Back-projecting and filtering are described above with respect to step S13.

Compressed sensing is a technique for acquiring or reconstructing a signal utilizing the prior knowledge that the signal is sparse or compressible. The three-dimensional ultrasound image may be reconstructed using techniques known in the art of compressed sensing. Reconstructing the image using compressed sensing may increase the resolution of the image displayed by an ultrasound system. Additionally, a value of minimizing noise using an L1 norm constraint may be calculated using Equation 3.

$$\bar{x} = arg_x \|y - Ax\|_{l_2} + \alpha |x|_{l_1}.$$  [Equation 3]

A de-noising technique may be used during reconstruction of the three-dimensional ultrasound image. The technique may be any technique used to suppress noise known in the art of noise reduction. Additionally, such a de-noising technique may be utilized during the generating and/or manipulating steps described above.

The projection-slice theorem may be used during reconstruction of the three-dimensional ultrasound image. This theorem states that each piece of projection data at some angle is the same as the Fourier transform of the multidimensional object at that angle. Using a range of data from a range of angles the actual image may be reconstructed by taking the inverse transform. For example, an inverse fast Fourier transform may be performed on the three-dimensional image data to reconstruct the three-dimensional ultrasound image.

Figure 4:
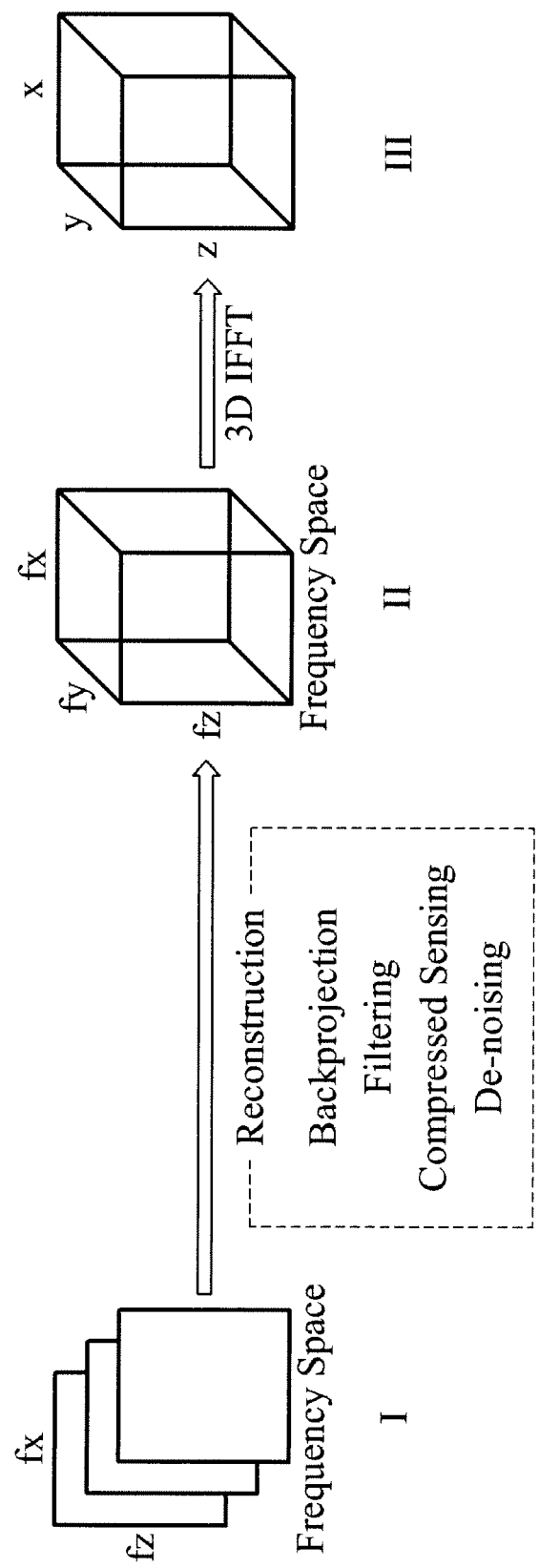
FIG. 4 is a conceptual diagram illustrating an exemplary step for reconstructing a three-dimensional image from the three-dimensional image data according to an embodiment of the present invention.

FIG. 4 is a conceptual diagram illustrating an exemplary step S15 for reconstructing a three-dimensional image from the three-dimensional image data according to an embodiment of the present invention.

At stage I, three-dimensional image data are illustrated as three manipulated two-dimensional images having various directivities in a frequency space. Between stages I and II, reconstructing the three-dimensional ultrasound image begins by back-projecting, filtering, applying compressed sensing, and/or de-noising the three-dimensional ultrasound image data as described above with respect to steps S13 and S15. Between stages II and III, the three-dimensional ultrasound image is reconstructed by calculating the three-dimensional inverse fast Fourier transformation of the three-dimensional image data as described above with respect to step S15. The reconstructed three-dimensional ultrasound image is illustrated in stage III.

Figure 5:
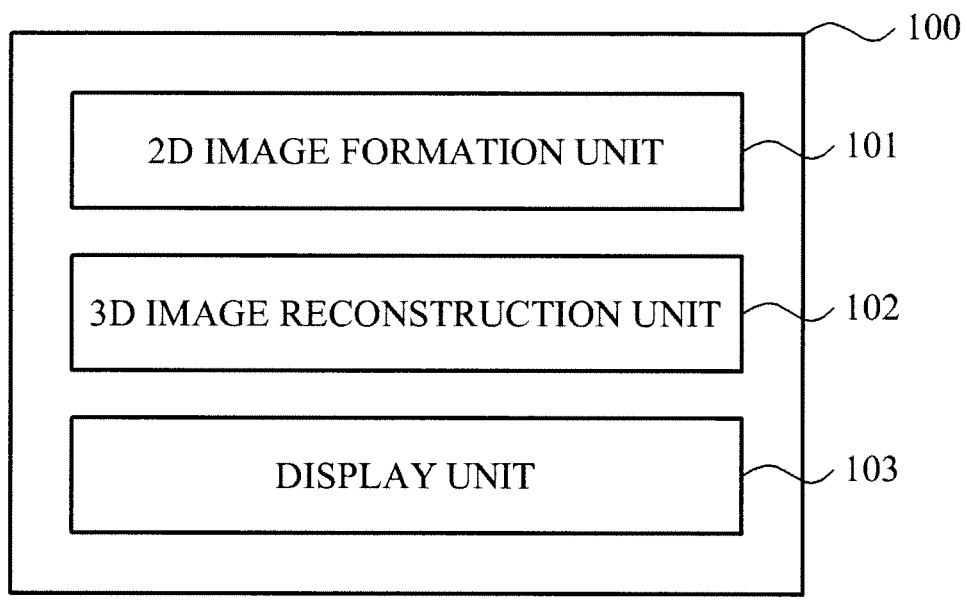
FIG. 5 is a block diagram illustrating an exemplary ultrasound system for reconstructing a three-dimensional ultrasound image according to an embodiment of the present invention.

FIG. 5 is a block diagram illustrating an exemplary ultrasound system 100 for reconstructing a three-dimensional ultrasound image according to an embodiment of the present invention. The ultrasound system 100 embodies the methods of the present invention and may include a two-dimensional image formation unit 101, a three-dimensional reconstruction unit 102, and a display unit 103.

The two-dimensional image formation unit 101 may be configured to generate a two-dimensional image having various directivities in a frequency space based on plane wave data transmitted from a plurality of directions by an ultrasound probe (not shown). This unit may use a fast Fourier transform and/or a lookup table to generate the two-dimensional image.

The three-dimensional image reconstruction unit 102 may be configured to manipulate the two-dimensional image to generate three-dimensional image data and to reconstruct a three-dimensional ultrasound image by performing an inverse fast Fourier transformation (IFFT) on the three-dimensional image data. This unit may use back-projection and/or filtering to manipulate the generated two-dimensional image and may use back-projection, filtering, compressed sensing, and/or de-noising to reconstruct the three dimensional image.

The display unit 103 may be configured to display the reconstructed three-dimensional ultrasound image.

The above-described embodiments of the present invention may be recorded in computer-readable media including program instructions to implement various operations embodied by a computer. The media may also include, alone or in combination with the program instructions, data files, data structures, and the like. The program instructions recorded on the media may be those specially designed and constructed for the purposes of the embodiments, or they may be of the kind well-known and available to those having skill in the computer software arts. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), RAM, flash memory, and the like. The media may also be a transmission medium such as optical or metallic lines, wave guides, etc. including a carrier wave transmitting signals specifying the program instructions, data structures, etc. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention, or vice versa.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A method for reconstructing a three-dimensional ultrasound image, the method comprising steps of:
    generating a two-dimensional image having various directivities in a frequency space based on plane wave data;
    manipulating the generated two-dimensional image to generate three-dimensional image data; and
    reconstructing a three-dimensional ultrasound image by performing an inverse fast Fourier transformation on the three-dimensional image data,
    wherein the step of manipulating the generated two-dimensional image comprises the step of back-projecting the generated two-dimensional image to generate the three-dimensional image data by taking a function defined on each of a plurality of lines in the generated two-dimensional image and projecting the function back over each line to generate the three-dimensional image data.

2. The method of claim 1, wherein the step of generating a two-dimensional image comprises generating the two-dimensional image using a fast Fourier transformation.

3. The method of claim 1, wherein the step of manipulating the generated two-dimensional image comprises the step of filtering the generated two-dimensional image before back-projecting.

4. The method of claim 1, wherein the step of reconstructing a three-dimensional ultrasound image further comprises the step of applying compressed sensing to the generated three-dimensional image data.

5. The method of claim 1, wherein the step of reconstructing a three-dimensional ultrasound image further comprises the step of de-noising the generated three-dimensional image data.

6. The method of claim 1, further comprising the step of transmitting, prior to the generating, manipulating and reconstructing steps, plane wave data from a plurality of directions via an ultrasound probe.

7. The method of claim 1, further comprising the step of displaying the reconstructed three-dimensional ultrasound image.

8. The method of claim 1, wherein the method is implemented using a computer-readable medium.

9. The method of claim 1, wherein the step of back-projecting the generated two-dimensional image includes the step of applying a dual Radon transform to the generated two-dimensional image.

10. An ultrasound system, comprising:
a two-dimensional image formation unit configured to generate a two-dimensional image having various directivities in a frequency space based on plane wave data;
a three-dimensional image reconstruction unit configured to manipulate the generated two-dimensional image to generate three-dimensional image data and reconstruct a three-dimensional ultrasound image by performing an inverse fast Fourier transformation on the three-dimensional image data,
wherein the three-dimensional image reconstruction unit is configured to apply back-projection to the generated two-dimensional image to generate the three-dimensional image data such that a function defined on each of a plurality of lines in the generated two-dimensional image is projected back over each line to generate the three-dimensional image data.

11. The system of claim 10, wherein the two-dimensional image formation unit is configured to apply a fast Fourier transformation to generate the two-dimensional image.

12. The system of claim 10, wherein the three-dimensional image reconstruction unit is configured to filter the generated two-dimensional image before applying the back-projection to the generated two-dimensional image.

13. The system of claim 10, wherein the three-dimensional image reconstruction unit further is configured to apply compressed sensing to the three-dimensional image data to reconstruct the three-dimensional ultrasound image.

14. The system of claim 10, wherein the three-dimensional image reconstruction unit is further configured to apply de-noising to the three-dimensional image data to reconstruct the three-dimensional ultrasound image.

15. The system of claim 10, further comprising an ultrasound probe configured to generate the plane wave data and transmit the plane wave data to the two-dimensional image formation unit.

16. The system of claim 10, further comprising a display unit configured to display the reconstructed three-dimensional ultrasound image.

17. The system of claim 10, wherein the three-dimensional image reconstruction unit is configured to apply back-projection to the generated two-dimensional image by applying a dual Radon transform to the generated two-dimensional image.

18. A computer readable medium comprising instructions that cause a computer processor to:
generate a two-dimensional image having various directivities in a frequency space based on plane wave data;
manipulate the generated two-dimensional image to generate three-dimensional image data; and
reconstruct a three-dimensional ultrasound image by performing an inverse fast Fourier transformation on the three-dimensional image data,
wherein the instructions causes the computer processor to apply back-projection to the generated two-dimensional image to generate the three-dimensional image data such that a function defined on each of a plurality of lines in the generated two-dimensional image is projected back over each line to generate the three-dimensional image data.

19. The computer readable medium of claim 18, wherein the instructions causes the computer processor to apply back-projection to the generated two-dimensional image by applying a dual Radon transform to the generated two-dimensional image.

* * * * *